US010569033B2

(12) United States Patent
Patton et al.

(10) Patent No.: US 10,569,033 B2
(45) Date of Patent: Feb. 25, 2020

(54) LIQUID DISPENSING AND METHODS FOR DISPENSING LIQUIDS

(71) Applicant: Dance Biopharm Inc., Brisbane, CA (US)

(72) Inventors: John S. Patton, Brisbane, CA (US); Ryan S. Patton, Brisbane, CA (US); Lisa Molloy, Brisbane, CA (US); Jim Fink, Brisbane, CA (US)

(73) Assignee: Dance Biopharm Inc., Brisbane, CA (US)

( * ) Notice: Subject to any disclaimer, the term of this patent is extended or adjusted under 35 U.S.C. 154(b) by 428 days.

(21) Appl. No.: 14/254,128

(22) Filed: Apr. 16, 2014

(65) Prior Publication Data
US 2014/0318533 A1 Oct. 30, 2014

Related U.S. Application Data

(60) Provisional application No. 61/812,547, filed on Apr. 16, 2013.

(51) Int. Cl.
*A61M 15/00* (2006.01)
*B05B 11/00* (2006.01)

(52) U.S. Cl.
CPC .... *A61M 15/0065* (2013.01); *A61M 15/0085* (2013.01); *B05B 11/0059* (2013.01); *A61M 2202/0468* (2013.01)

(58) Field of Classification Search
CPC ........ A61M 11/00; A61M 11/001–008; A61M 11/02–08; A61M 13/00;
(Continued)

(56) References Cited

U.S. PATENT DOCUMENTS 4,227,615 A 10/1980 Flick
4,294,407 A * 10/1981 Reichl ................. A61M 11/005
128/200.16
(Continued)

FOREIGN PATENT DOCUMENTS

CN 1387447 A 12/2002
CN 102740915 A 10/2012
(Continued)

OTHER PUBLICATIONS

International Preliminary Report on Patentability for International I Patent Application No. PCT/US2014/034356, dated Oct. 29, 2015, 11 pages.
(Continued)

*Primary Examiner* — Michael J Tsai
*Assistant Examiner* — Ned T Heffner
(74) *Attorney, Agent, or Firm* — Kilpatrick Townsend & Stockton LLP

(57) ABSTRACT

A dispenser for supplying a metered volume of a liquid medicament to an aerosolizing device. The dispenser may include a container having a proximal end and a distal end, wherein the container is configured to store a volume of liquid medicament. The dispenser may also include a dispensing mechanism coupled to the distal end of the container. The dispensing mechanism may have a distal end terminating in a tip through which the liquid medicament is dispensed. The dispensing mechanism operates to dispense a metered volume of the liquid medicament from the tip each time the dispensing mechanism is operated. The distal end of the dispensing mechanism includes an interface that interacts with a housing of an inhaler to limit an insertion depth of the tip into an opening the housing.

22 Claims, 11 Drawing Sheets

(58) Field of Classification Search
CPC .... A61M 15/00–0011; A61M 15/0028; A61M 15/0065–0078; A61M 15/0085; A61M 15/009; A61M 15/06; A61M 15/08; A61M 15/085; A61M 16/18–186; A61M 31/00; B61D 83/14–208; B61D 83/28–303; B61D 83/44
USPC ....... 222/1, 23, 50, 51, 36–38, 402.1, 321.9, 222/321.7, 575; 604/295, 296, 298, 299
See application file for complete search history.

(56) References Cited

U.S. PATENT DOCUMENTS

| | | | |
|---|---|---|---|
| 4,637,528 | A | 1/1987 | Wachinski et al. |
| 5,586,550 | A | 12/1996 | Ivri et al. |
| 5,758,637 | A | 6/1998 | Ivri et al. |
| 5,938,117 | A | 8/1999 | Ivri |
| 6,014,970 | A | 1/2000 | Ivri et al. |
| 6,085,740 | A * | 7/2000 | Ivri ...................... A61M 11/005 128/200.14 |
| 6,205,999 | B1 | 3/2001 | Ivri et al. |
| 6,250,209 | B1 | 6/2001 | Fuchs |
| 6,260,549 | B1 * | 7/2001 | Sosiak ............... A61M 15/0065 128/200.14 |
| 6,302,101 | B1 * | 10/2001 | Py .......................... A61M 11/06 128/200.14 |
| 6,427,682 | B1 | 8/2002 | Klimowicz et al. |
| 6,467,476 | B1 | 10/2002 | Ivri et al. |
| 6,540,153 | B1 | 4/2003 | Ivri |
| 6,540,154 | B1 | 4/2003 | Ivri et al. |
| 6,629,646 | B1 | 10/2003 | Ivri |
| 6,640,804 | B2 | 11/2003 | Ivri et al. |
| 6,755,189 | B2 | 7/2004 | Ivri et al. |
| 6,814,071 | B2 | 11/2004 | Klimowicz et al. |
| 6,921,020 | B2 | 7/2005 | Ivri |
| 6,926,208 | B2 | 8/2005 | Ivri |
| 7,108,197 | B2 | 9/2005 | Ivri |
| 6,978,941 | B2 | 12/2005 | Litherland et al. |
| 6,981,618 | B2 * | 1/2006 | Reisinger ............... A61C 5/062 222/326 |
| 7,032,590 | B2 | 4/2006 | Loeffler |
| 7,040,549 | B2 | 5/2006 | Ivri et al. |
| 7,066,398 | B2 | 7/2006 | Borland et al. |
| 7,083,112 | B2 | 8/2006 | Ivri |
| 7,100,600 | B2 | 9/2006 | Loeffler et al. |
| 7,174,888 | B2 | 2/2007 | Ivri et al. |
| 7,195,011 | B2 | 3/2007 | Loeffler et al. |
| 7,628,339 | B2 | 12/2009 | Ivri et al. |
| 7,845,346 | B2 * | 12/2010 | Langford ............ A61M 15/009 128/200.14 |
| 2002/0043262 | A1 | 4/2002 | Langford et al. |
| 2005/0121024 | A1 | 6/2005 | Langford et al. |
| 2006/0255072 | A1 | 11/2006 | Hagin et al. |
| 2007/0102451 | A1 | 5/2007 | Pruvot et al. |
| 2011/0168170 | A1 | 7/2011 | Patton et al. |
| 2011/0168172 | A1 * | 7/2011 | Patton ............... A61M 15/0085 128/200.23 |
| 2016/0354795 | A1 | 12/2016 | Taberlet et al. |

FOREIGN PATENT DOCUMENTS

| | | |
|---|---|---|
| EP | 0 446 513 A1 | 9/1991 |
| EP | 0 571 280 A1 | 11/1993 |
| KR | 10-2012-0085767 A | 8/2012 |
| RU | 2669930 C2 | 10/2018 |
| WO | 2004/028607 A1 | 4/2004 |
| WO | 2008/097645 A1 | 8/2008 |
| WO | 2009/086009 A1 | 7/2009 |
| WO | WO2009/086009 A1 | 7/2009 |
| WO | 2011/077123 A1 | 6/2011 |
| WO | 2013/158353 A1 | 10/2013 |

OTHER PUBLICATIONS

International Search Report and Written Opinion of PCT/US2014/034356 dated Sep. 11, 2014, 13 pages.
European Patent Application No. 14 78 5659.5, "Extended European Search Report" dated Oct. 17, 2016, all pages.
Office Action dated May 16, 2017 in Chinese Application 201480034163.X, all pages.
AU application No. 2014253997 received a First Examination Report dated Feb. 6, 2017, 6 pages.
EP 14785659.5 received an Office Action, dated Sep. 22, 2017, all pages.
CN201480034163.X received an Office Action dated Oct. 29, 2018, 9 pages.
AU2014253997 received a Second Examination Report dated Sep. 17, 2018, 3 pages.

* cited by examiner

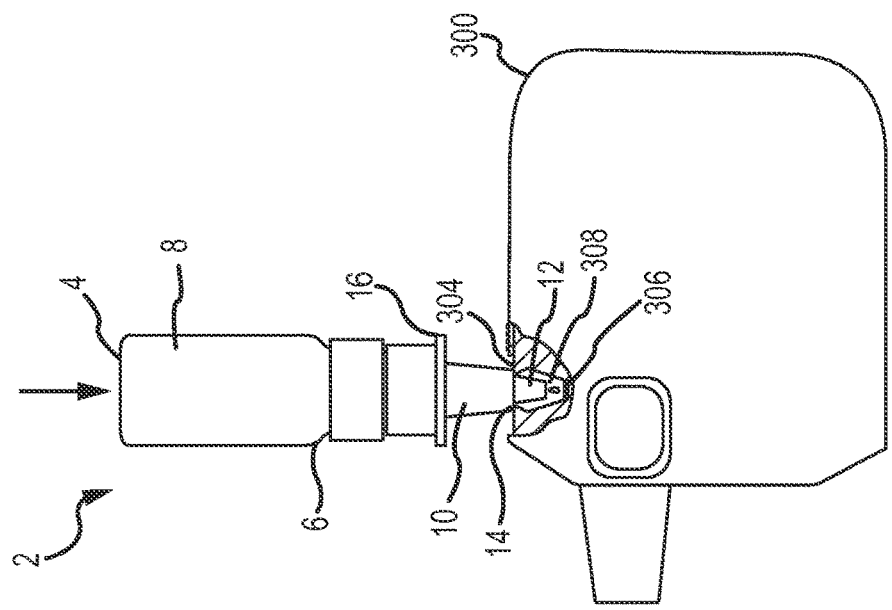
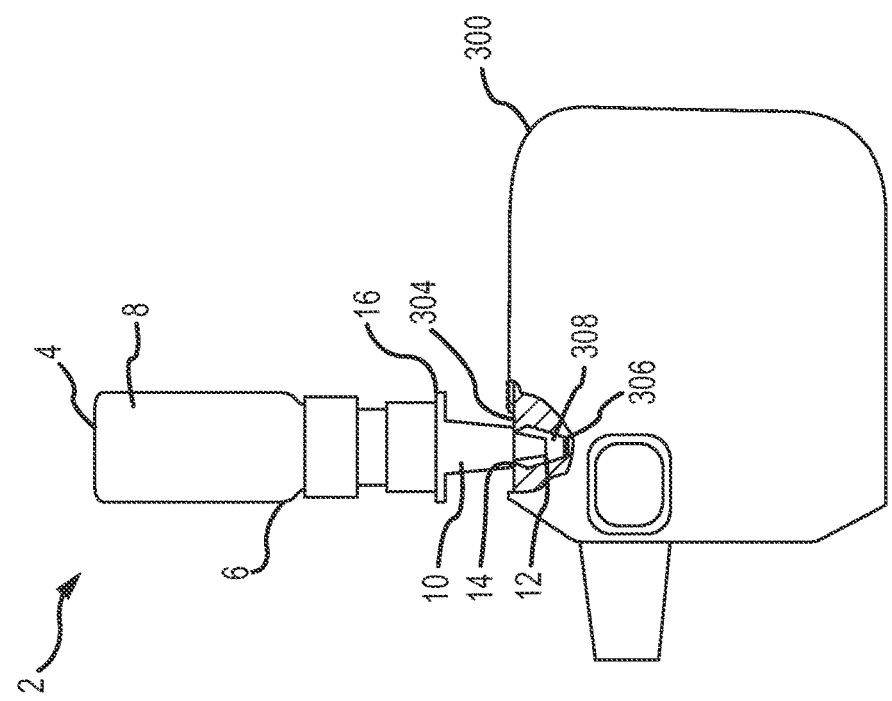

LIQUID DISPENSING AND METHODS FOR DISPENSING LIQUIDS

CROSS REFERENCE TO RELATED APPLICATIONS

This nonprovisional application claims priority from U.S. Provisional Application No. 61/812,547, filed on Apr. 16, 2013, the complete disclosure of which is herein incorporated by reference.

BACKGROUND OF THE INVENTION

Various types of dispensers exist for delivering a measured volume of a liquid into an aerosolizing apparatus, such as the inhaler apparatus described in co-pending U.S. application Ser. No. 13/830,511, entitled "METHODS AND SYSTEMS FOR SUPPLYING AEROSOLIZATION DEVICES WITH LIQUID MEDICAMENTS" incorporated herein by reference. One aspect of such dispensers is the desire to maximize the amount of liquid medicament that can be dispensed. Due to the large costs associated with many types of medicaments, there is a strong desire to not waste any of the liquid. Additionally, it is important to provide an accurate dose of medicament to a user. Improvements in delivering the entire supply of liquid medicament while providing accurate doses to inhalers for subsequent aerosolizing are desired.

BRIEF SUMMARY OF THE INVENTION

The terms "invention," "the invention," "this invention" and "the present invention" used in this patent are intended to refer broadly to all of the subject matter of this patent and the patent claims below. Statements containing these terms should not be understood to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to the entire specification of this patent, all drawings and each claim.

One particular embodiment provides a dispenser for supplying a metered volume of a liquid medicament to an aerosolizing device. The dispenser may include a container having a proximal end and a distal end, wherein the container is configured to store a volume of liquid medicament. The dispenser may also include a dispensing mechanism coupled to the distal end of the container. The dispensing mechanism may have a distal end terminating in a tip through which the liquid medicament is dispensed. The dispensing mechanism operates to dispense a metered volume of the liquid medicament from the tip each time the dispensing mechanism is operated. The distal end of the dispensing mechanism includes an interface that interacts with a housing of an inhaler to limit an insertion depth of the tip into an opening the housing.

In some embodiments, the dispensing mechanism includes housing cap having a bottom surface that is sloped toward an aperture to aid in the draining of liquid medicament from the container into the dispensing mechanism. In some embodiments, the interface comprises a seat. In other embodiments, the interface comprises a shoulder, wherein the shoulder and the tip each have a diameter. The diameter of the shoulder is larger than the diameter of the tip. In some embodiments, the container also includes an indicator line positioned near the proximal end that indicates to a user when there is insufficient liquid for a proper dispensing, i.e., when the container should no longer be used. A bottom surface of the proximal end may be sloped such that the indicator line is raised a distance from the proximal end.

In another aspect, the present invention provides a method for manufacturing a dispenser for supplying a metered volume of a liquid medicament to an aerosolizing device. The method can include providing a container having a proximal end and a distal end. The container is configured to store a volume of liquid medicament. The method may also include providing a dispensing mechanism that operates to dispense a metered volume of the liquid medicament from a tip of a distal end of the dispensing mechanism each time the dispenser is operated. The distal end of the dispensing mechanism includes an interface that interacts with a housing of an inhaler to limit an insertion depth of the tip into an opening of the housing. In some embodiments, the interface includes a shoulder, and the shoulder and the tip each have a diameter. The diameter of the shoulder is larger than the diameter of the tip.

In some embodiments, the dispensing mechanism includes a housing cap having a bottom surface that is sloped towards an aperture to aid in the draining of liquid medicament from the container into the dispensing mechanism. The dispenser may be compressible such that the dispenser delivers a metered volume of liquid medicament upon application of a compressive force. In one embodiment, the container further includes an indicator line positioned near the proximal end that indicates to a user when there is insufficient liquid for dispensing a unit dose. A bottom surface of the proximal end may be sloped such that the indicator line is raised a distance from the proximal end.

In another aspect, the present invention provides a method for supplying a metered volume of liquid medicament to an aerosolizing device. The method can include providing a dispenser having a container having a proximal end and a distal end. The container may include a volume of liquid medicament. The dispenser may have a dispensing mechanism coupled to the distal end of the container. The dispenser mechanism may have a distal end having an interface and terminating in a tip. The method may include providing an inhaler having a housing with a mouthpiece. The inhaler may also include an opening in the housing configured to receive the tip of the dispenser and a vibratable mesh spaced a distance from the opening that is configured to aerosolize the metered volume of liquid medicament. The method may include inserting the tip into the opening of the inhaler until the interface of the distal end contacts the housing outside of the opening to limit an insertion depth of the tip to maintain the tip a distance from the vibratable mesh. The method may also include compressing the dispenser to deliver a metered volume of the liquid medicament from the tip to the vibratable mesh.

In some embodiments, compressing the dispenser is performed by applying a compressive force to both the inhaler and the dispenser. The method may optionally include placing the inhaler on a support surface and compressing the dispenser by applying a compressive force to the dispenser. In some embodiments, the inhaler further includes a cover that seals the opening and the vibratable mesh. The method may also include moving the cover to expose the opening and the vibratable mesh. In some embodiments, the dispensing mechanism includes a housing cap that includes a bottom surface that is sloped toward the aperture such that when the dispenser is inverted the liquid medicament is directed into the container may include an indicator line positioned near the proximal end that indicates to a user when there is insufficient liquid for recommended dispensing. In some embodiments, the interface contacts the housing such that the tip is maintained at a distance from the mesh such that the tip is not in contact with the dispensed metered volume of the liquid medicament.

In another aspect, the present invention provides a dispenser for supplying a metered volume of a liquid medicament to an aerosolizing device. The dispenser can include a container having a proximal end and a distal end. The container may be configured to store a volume of liquid medicament. The container may also include an indicator mark positioned near the proximal end that indicates to a user when there is insufficient liquid for supplying a unit dose to the aerosolizing device. In this way, the user knows when the container should be replaced with new container. The dispenser may include a dispensing mechanism coupled to the distal end of the container. The dispensing mechanism may include a distal end terminating in a tip through which the liquid medicament is dispensed. The dispensing mechanism may operate to dispense a metered volume of the liquid medicament from the tip each time the dispensing mechanism is operated. The distal end of the dispensing mechanism may include an interface that interacts with a housing of an inhaler to limit an insertion depth of the tip into an opening of the housing.

In some embodiments, the indicator mark may be fashioned as a top portion with a top shape and a bottom portion with a certain shape. The top portion and the bottom portion are separated by a certain displace so that a transparent portion or region is visible between the top portion and the bottom portion. When a level of the liquid medicament falls below the transparent portion there may be insufficient liquid for recommended dispensing. In some embodiments, the top portion and the bottom portion may be in the shape of half circles and the transparent portion may include a clear line. In some embodiments, the top portion and the bottom portion may be in the shape of rectangles and the transparent portion may include a clear line between the two rectangles. In some embodiments, the indicator mark may be shaped such that when a level of the liquid medicament falls below a bottom edge of the indicator mark there is insufficient liquid for a recommended dispensing, indicating that the container needs to be replaced. In some embodiments, the indicator mark may be in the form of a horizontal line extending along at least a portion of one or more sides of the container. In some embodiments, the bottom surface of the proximal end of the container may be sloped such that the indicator line may be raised a distance from the proximal end.

BRIEF DESCRIPTION OF THE DRAWINGS

Illustrative embodiments of the present invention are described in detail below with reference to the following drawing figures:

FIG. 8 is a side view of the dispenser of FIG. 1 in an uncompressed state and interfaced with an inhaler.

FIG. 9 is a side view of the dispenser of FIG. 1 dispensing a liquid into an inhaler.

DETAILED DESCRIPTION OF THE INVENTION

Certain aspects of the invention relate to techniques for dispensing a liquid medicament into an aerosolizing apparatus, also referred to as an inhaler or an aerosolizer. Although useful with a wide variety of aerosolizing devices, in some cases the liquid will be dispensed into an aerosolizing apparatus comprising a housing defining a dispensing outlet or mouthpiece, a vibratable membrane or mesh having a front face exposed at the outlet and a rear face for receiving a liquid to be dispensed, and a vibrating mechanism connected to the housing and operable to vibrate the membrane to dispense aerosol of the liquid through the membrane.

A variety of containers or dispensers may be used to store the liquid medicament, then to deliver a metered volume of the liquid into a reservoir or directly onto the vibratable membrane where it will contact the rear face of the membrane. In this way, a metered volume of liquid is dispensable at the outlet or mouthpiece by operating the vibrating mechanism for an operating period sufficient to completely aerosolize the metered volume at the rear face. The containers or dispensers will typically have a sealed region where the liquid is stored and a mechanism for dispensing a metered volume of liquid each time the mechanism is operated. For example, the container may be compressed or pumped to eject a droplet of a known volume.

Figure 1:
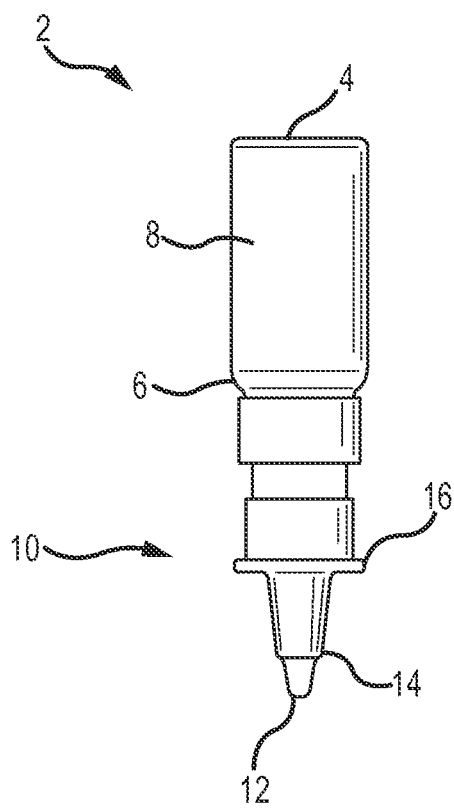
FIG. 1 is a side view of a dispenser in an uncompressed state according to one embodiment of the invention.
Figure 2:
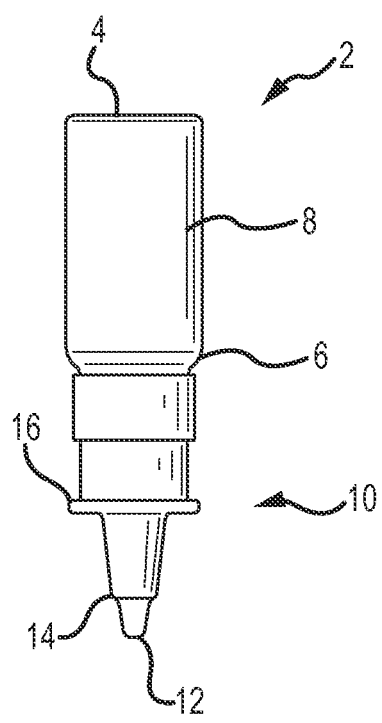
FIG. 2 is a side view of the dispenser of FIG. 1 in a compressed state.
Figure 3:
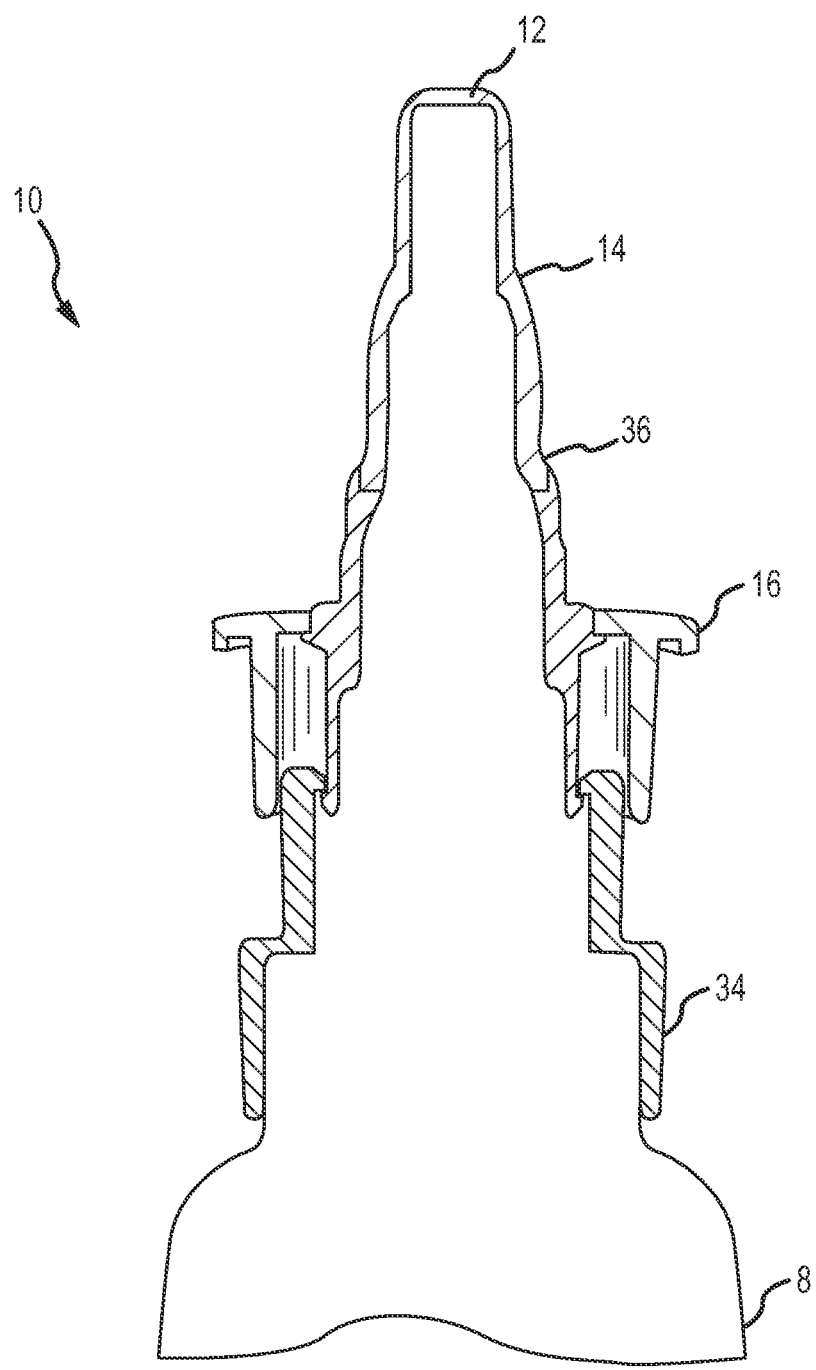
FIG. 3 is a cross-section of the dispensing mechanism of the dispenser of FIG. 1.
Figure 5:
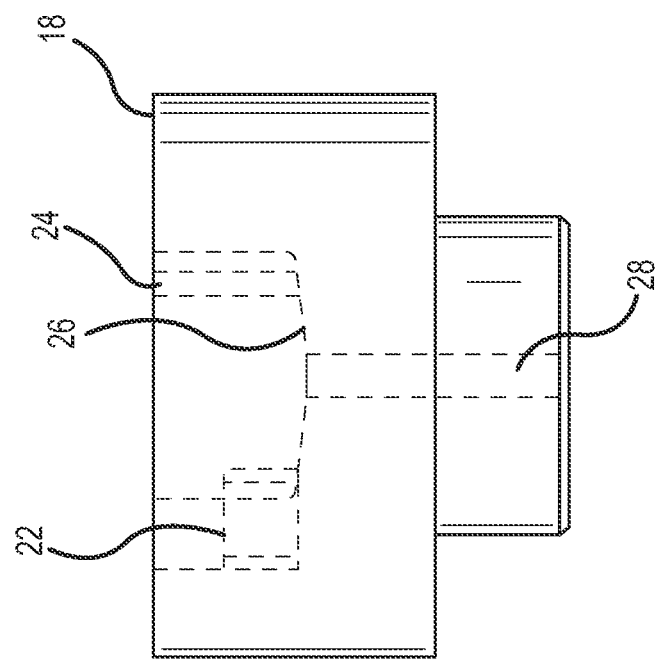
FIG. 5 is a side cross-section view of a housing cap of FIG. 4.
Figure 4:
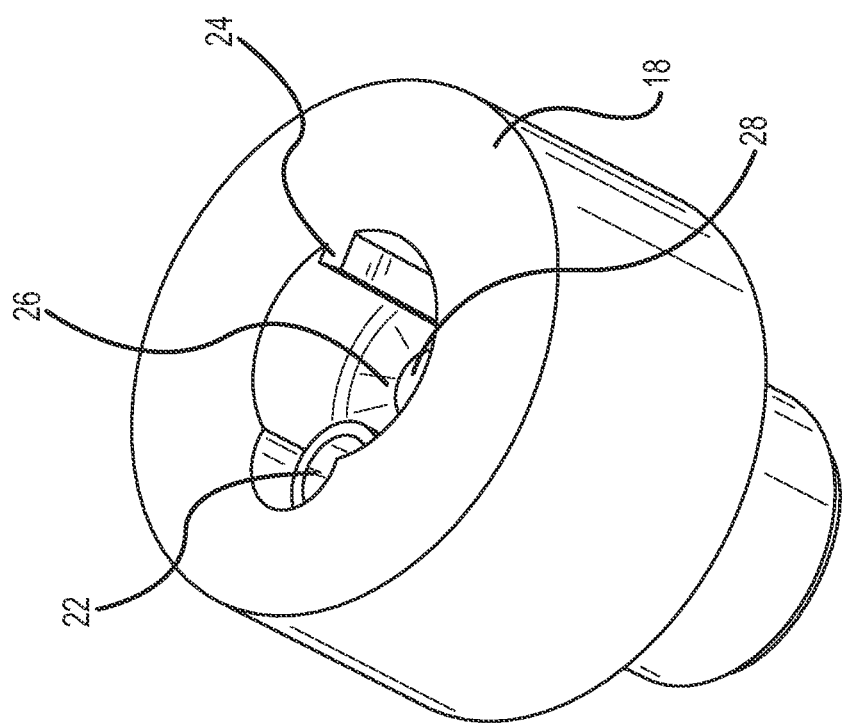
FIG. 4 is an isometric view of a housing cap of the dispenser of FIG. 1.
Figure 6:
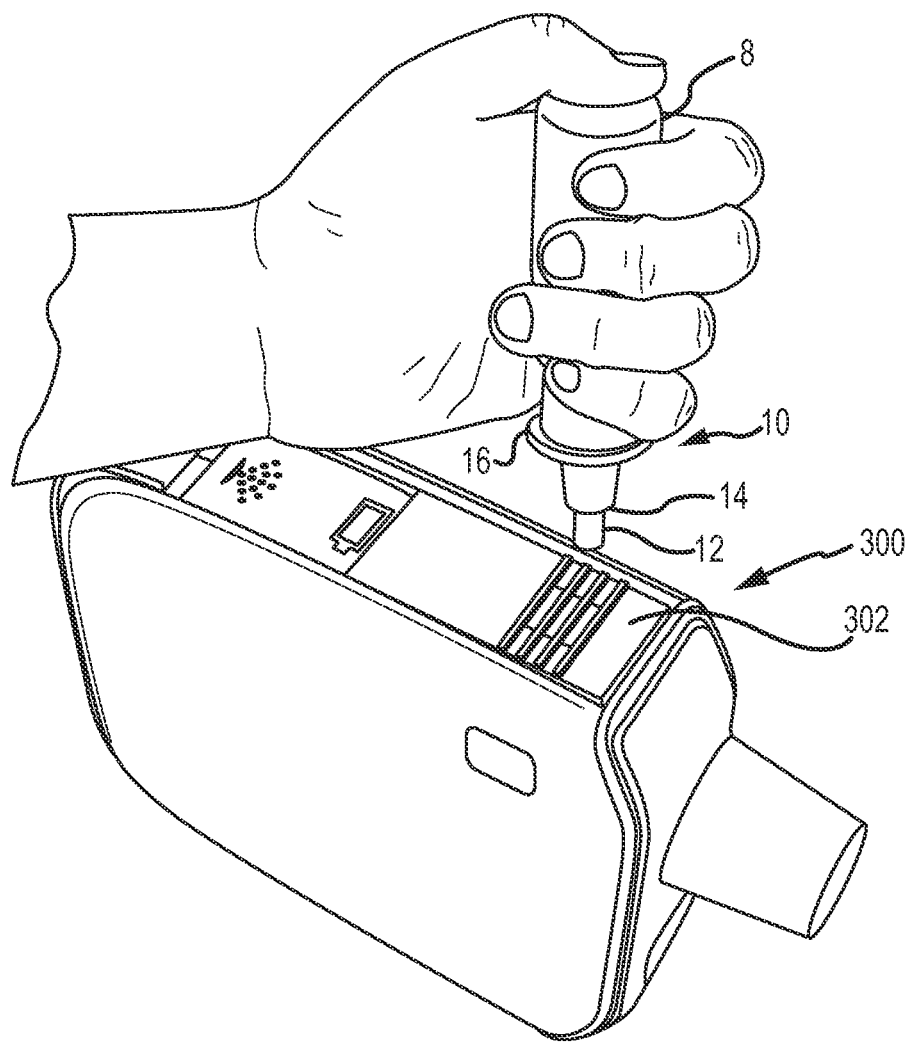
FIG. 6 is an isometric view of a user holding the dispenser of FIG. 1 in an uncompressed position.
Figure 7:
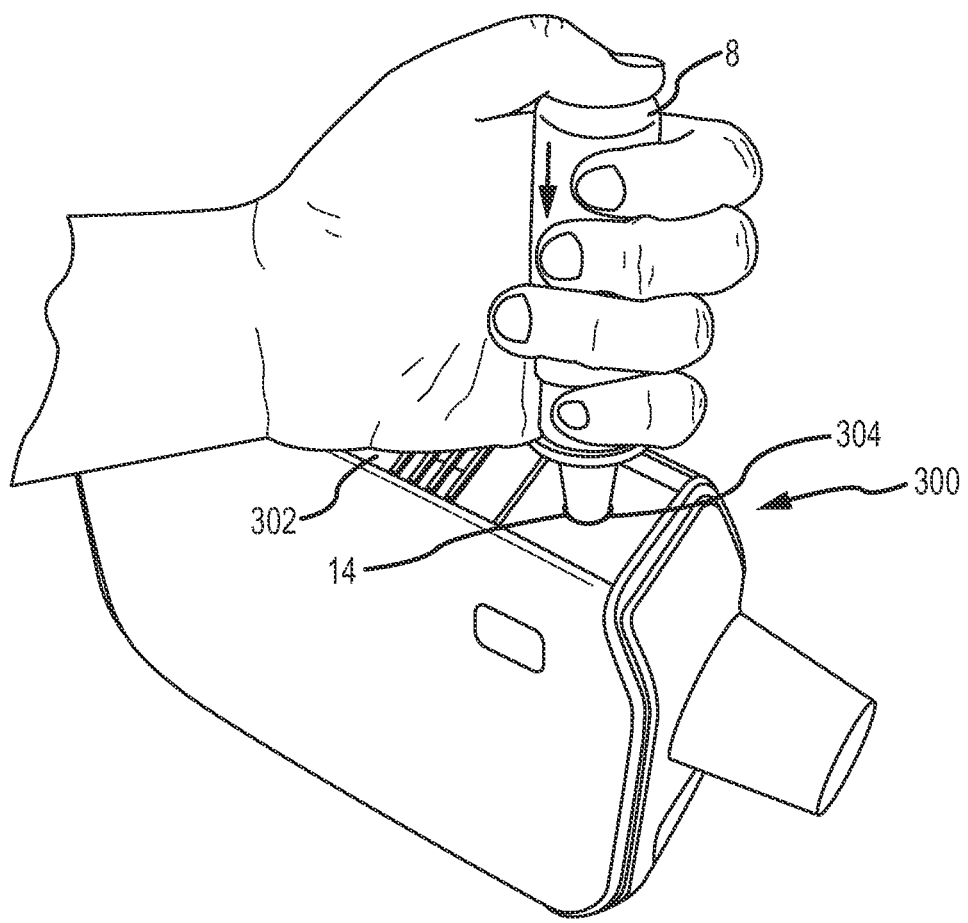
FIG. 7 is an isometric view of a user holding the dispenser of FIG. 1 in a compressed position.
Figure 10:
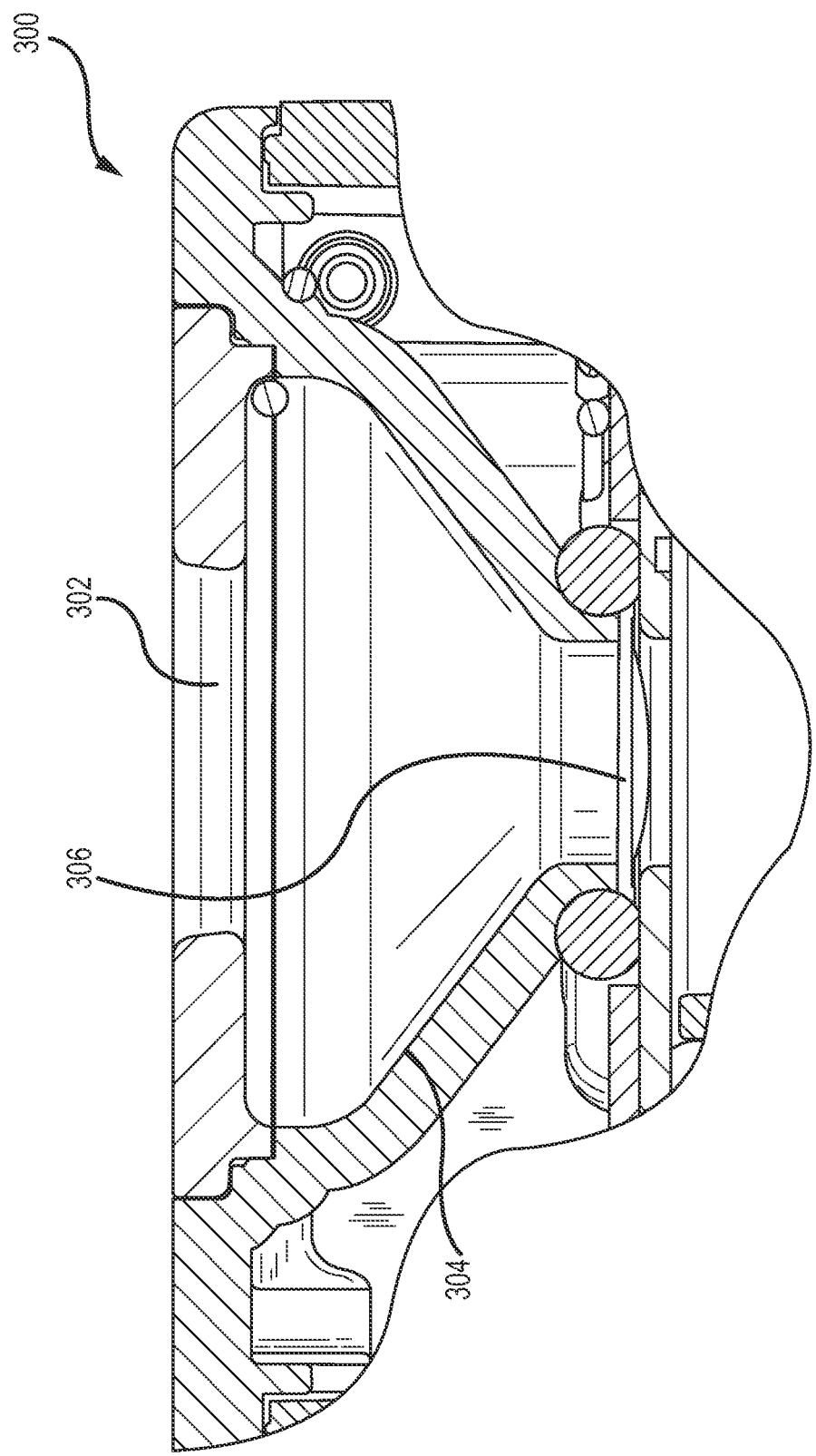
FIG. 10 shows a cross-section of a chamber and vibratable mesh of an aerosol generator for receiving the liquid medicament according to embodiments of the invention.
Figure 11:
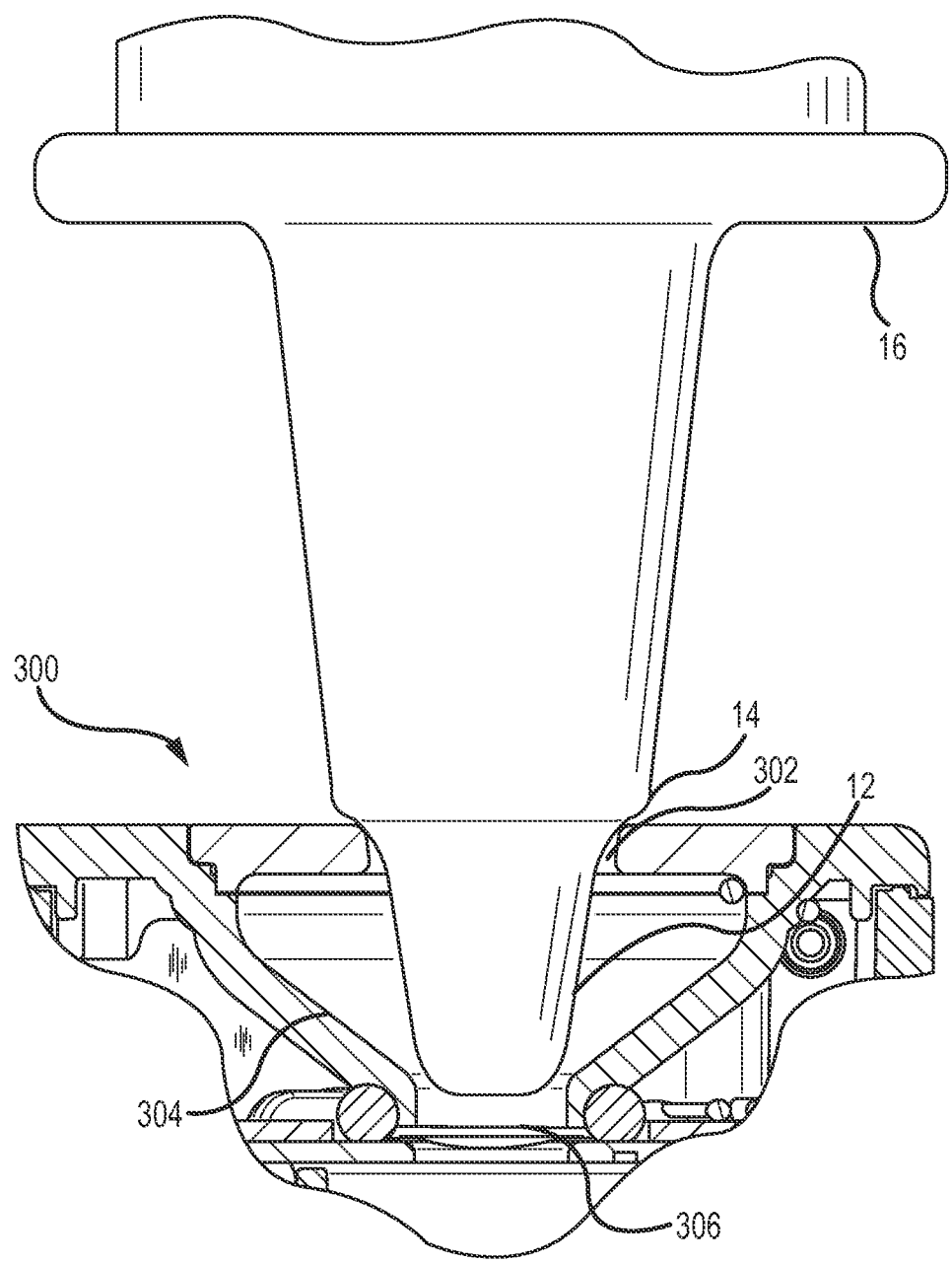
FIG. 11 shows a dispenser interfaced with an opening of an aerosol generator according to embodiments of the invention.
Figure 12:
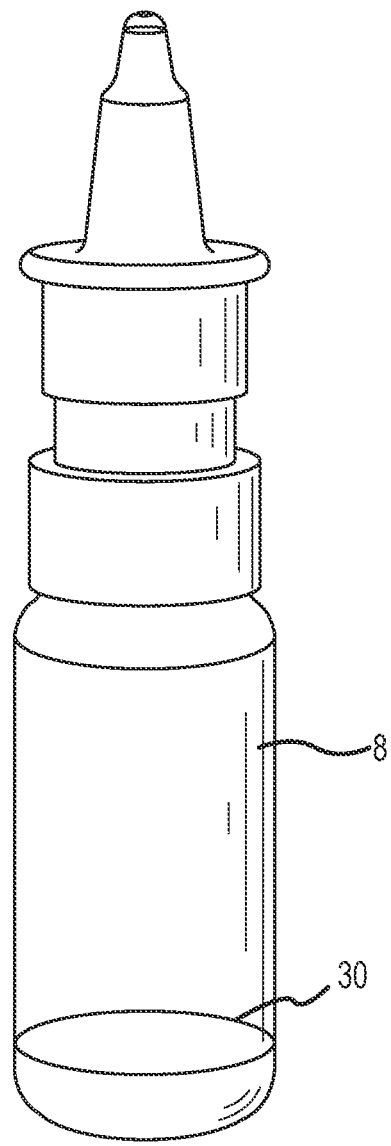
FIG. 12 is an embodiment of a dispenser having a last-use mark.
Figure 15:
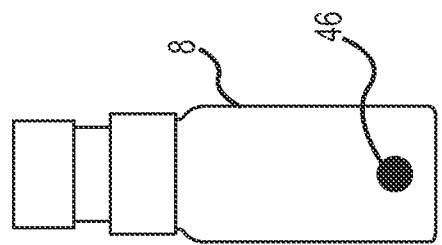
FIG. 15 is an embodiment of a dispenser having a last-use mark.
Figure 14:
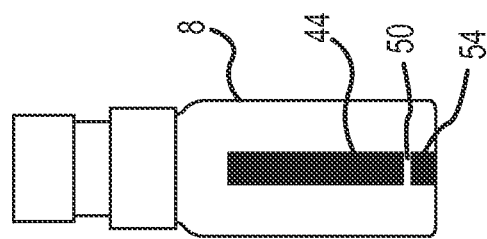
FIG. 14 is an embodiment of a dispenser having a last-use mark.
Figure 13:
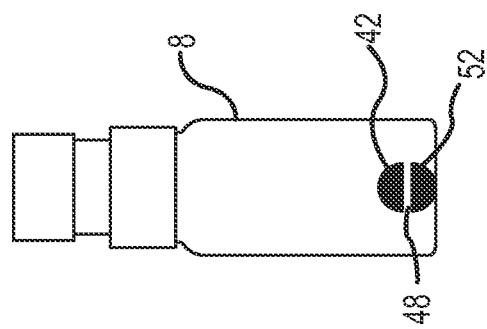
FIG. 13 is an embodiment of a dispenser having an easy to read last-use mark.

Referring now to FIGS. 1 and 2, liquid to be aerosolized is stored in a dispenser 2. Dispenser 2 may conveniently be described in terms of a vial or container 8 and a dispensing mechanism 10. Container 8 has a proximal end 4 and a distal end 6. Container 8 stores a volume of liquid medicament in a sterile environment. A variety of liquid medicaments may be dispensed from dispenser 2. For example, the liquid medicament may comprise an insulin formulation, such as a preservative free insulation, including any of those described in U.S. Patent Publication No. 2011/0168170, incorporated by reference herein. Other liquid medicaments may also be dispensed. For example, such medicaments could include other protein formulations, asthma and COPD treatments, vaccines, and pain relief treatments.

Distal end 6 can be configured to mate with dispensing mechanism 10, which tapers off, forming a tip 12. Dispensing mechanism 10 is configured to dispense a metered volume of liquid medicament when operated. Dispensing may be achieved by pumping or compressing a portion of dispensing mechanism 10. Dispensing mechanism 10 can include an interface 14, such as shoulder 14 or other seat or seating mechanism positioned between tip 12 and a flange 16. Shoulder 14 can have a larger diameter than tip 12. In some embodiments, shoulder 14 may be a shaped step, such as an annular step, that serves as a stop to limit a maximum depth of insertion of tip 12 into an aerosol device. Shoulder 14 is inset by a distance that is sufficient so that it not only serves as a stop but also permits tip 12 to seat within an opening an aerosol device in a stable position that is generally vertical to a top surface of an aerosol device. The tip 12 is seated within the opening when a surface of the shoulder 14 is flush in contact with a surface of a housing of the aerosol device that defines the opening of the device and the tip extends through the opening. In such a seated position, any liquid medicament within the dispenser will be drawn downward to the tip 12. Although shown with shoulder 14, other seating mechanisms could be used, such as a taper that matches with the taper of an opening in an aerosol device, protruding tabs or wings, detents, and the like. As another option, the seating mechanism may be keyed such that tip 12 can only be received by the opening in the aerosol device at a certain orientation. The shoulder 14 can set the insertion depth of the tip by contacting a surface outside of the opening in the aerosol device such that the tip 12 cannot be inserted further into the device.

Flange 16 can be used by a patient to apply force to actuate dispensing mechanism 10. Actuation of dispensing mechanism 10 allows tip 12 to be moved relative to proximal end 4, thus compressing dispenser 2. In so doing, each time dispenser 2 is compressed (or "pumped") a metered volume of liquid is ejected from tip 12. For example, FIG. 1 shows dispenser 2 in an uncompressed state. In FIG. 2, a force is applied to compress dispenser 2 and eject the droplet.

Referring to FIG. 3, the outer surface or housing of dispensing mechanism 10 is shown in cross section. For convenience of illustration, the interior of the housing of dispensing mechanism 10 is not shown. To dispense a metered volume, dispensing mechanism includes a housing cap that fastens dispensing mechanism 10 to a container, such as container 8 described herein. This coupling can be achieved in a variety of ways including, but not limited to, snap fasteners, screw on fasteners, and the like. A gasket or O-ring can be included at the junction of container and housing cap to form an airtight seal between the two components. The dispensing mechanism 10 can include a fixed portion 34 and a slidable portion 36. Fixed portion 34 can be more proximal to the container than slidable portion 36 and is fixed in position relative to the container. Slidable portion 36 may be coupled with fixed portion 34. The interface between the fixed portion 34 and slidable portion 36 can include a spring that biases the slidable portion 36 in an uncompressed state away from the container. Upon compressing the slidable portion 36 toward the fixed portion 34, a valve within the dispensing mechanism 10 is opened to prime the pump, allowing a volume of the liquid medicament to fill a metering chamber. When filled, this chamber holds a metered dose of the liquid medicament. The dispensing mechanism 10 may deliver the metered dose from tip 12 upon compression when primed. Shoulder 14 may be positioned against a surface of a housing of an aerosol device to limit an insertion depth of tip 12.

Referring to FIGS. 4 and 5, housing cap 18 is described. Housing cap 18 may optionally receive an air return filter 22 and can include a notch 24 opposite air return filter 22 for aiding in assembly. An aperture or hole 28 may be included on bottom surface 26. Hole 28 helps to extract the last amounts of liquid medicament from container 8 when dispenser 2 is inverted for dispensing the liquid into an aerosol device. In some embodiments, multiple holes may be positioned on opposite sides of the bottom surface, or optionally at positions such that each hole is spaced at the same angle relative to each of the nearest other hole or holes. Additionally bottom surface 26 can be sloped toward the hole 28 to further aid in draining the final remnants of liquid from container 8 as shown in FIG. 5. Hole 28 is sized to be sufficiently large to facilitate drainage of the liquid in the container and into the dispensing mechanism.

Some embodiments contain only a single hole 28 positioned on bottom surface 26. This arrangement can help keep air out of dispensing mechanism 10 upon tilting dispenser 2 in a way that would otherwise result in a second hole being exposed to air while the first hole 28 was submerged in liquid medicament. By keeping excess air out of dispensing mechanism 10, more reliable dosages can be achieved throughout the life of dispenser 2.

One exemplary technique for operating dispenser 2 is illustrated in FIGS. 6-11. In FIGS. 6 and 7, dispenser 2 is grasped with one hand, such that the four fingers wrap around dispenser 2, mostly about container 8. By using four fingers to grasp dispenser 2, a firm grip is achieved so that dispenser 2 may easily be pumped to eject the liquid. Further, the person's thumb may rest on proximal end 4 to apply a further compressive force. With the proper grip, a cover 302 on inhaler 300 may be slid back and tip 12 placed into opening 304 as shown in FIG. 7. In this inverted position with proximal end 4 above distal end 6, liquid may drain from container 8 into dispensing mechanism 10. Shoulder 14 is wider than opening 304 so as to set an insertion depth of the tip 12 to prevent tip 12 from coming into contact with a membrane or mesh 306 that is spaced a distance from opening 302. As best seen in FIGS. 8, 9, and 11, shoulder 14 may be designed so that tip 12 is sufficiently spaced-apart from mesh 306 so that when the full metered amount of the liquid is dispensed into a reservoir 308, tip 12 does not come into contact with the dispensed liquid. In this way, when dispenser 2 is removed from inhaler 300, it will not remove any of the dispensed liquid. Oftentimes, tip 12 will be spaced apart from mesh 306 by a distance that is in the range from about 5 mm to about 20 mm. Tip 12 may also be tapered, such as to match the taper of reservoir 308. The taper of reservoir 308 facilitates delivery of all the dispensed liquid onto the rear face of mesh 306, and the tapering of tip 12 prevents tip 12 from coming into contact with the walls of reservoir 308. Another exemplary technique for operating dispenser is to use the palm of the hand to exert pressure on the dispenser while docked to the aerosol device.

As best shown in FIG. 7, with tip 12 in place, the user presses container 8 toward tip 12. The user may press container 8 towards tip by wrapping the user's fingers around sides of the dispenser 2 and placing a thumb on proximal end 4 to apply the compressive force. In other embodiments, a user may position the tip 12 in place within the inhaler 300 and apply a compressive force to the proximal end 4 with the user's palm. While the dispenser 2 is compressed, inhaler 300 is held in place. This causes dispenser 2 to compress. In turn, the dispensing mechanism permits a metered amount of liquid to be dispensed from tip 12 and into reservoir 308 or onto the vibratable mesh 306. Each time container 8 is pressed downward, or pumped, another metered amount of liquid is ejected from tip 12. This maneuver is performed as many times as is needed in order to supply the prescribed dosage into reservoir 308.

By holding dispenser 2 in the manner shown, this pumping action may easily occur. This is in contrast to a nasal spray dispenser, which is typically actuated in an upright manner by carefully and simultaneously compressing the distal end with the middle and index finger (with the tip extending between the fingers) to the proximal end of the dispenser container, which is held under equal pressure by the thumb. With this type of nasal sprayer, the spray occurs when sufficient pressure is applied equally to both ends. In contrast, dispenser 2 can be easily actuated by applying pressure solely to the proximal end 4 of the dispenser 2 when the tip 12 is engaged with inhaler 300. Inhaler 300 and mating features are constructed so that a metered volume of medicament is consistently delivered from dispenser 2 into inhaler 300. The user may compress the dispenser 2 with unregulated pressure, provided the force is greater than or equal to that required to compress dispenser 2 throughout its full range. If inhaler 300 is loaded while placed on a table or any other freely supported surface, the apparent force required to compress dispenser 2 into inhaler 300 to the point of actuation is reduced by 50% when compared to the amount of force required to disperse a volume of liquid when holding both inhaler 300 and dispenser 2 (without the aid of a support surface). After dispersing the desired volume of liquid medicament, dispenser 2 may be removed from opening 304 and stored for future use. The cover 302 may be returned to a closed position to seal the opening 304, mesh 306, and reservoir 308. The cover 302 may be left open for some period of time to ensure that inner components of the inhaler 300, such as the mesh 306, are exposed to air to sufficiently dry before cover 302 is closed. Exemplary unit volumes that may be dispensed with each pump may be in the range from about 20 to about 100 microliters.

FIGS. 10 and 11 show close up views of the opening 300, the reservoir 304, and vibratable mesh of inhaler 300. The sides of reservoir 304 are tapered such that any dispensed liquid medicament that does not fall onto the vibratable mesh 306 is directed onto the mesh 306. As seen in FIG. 11, the interface 14 limits the insertion depth of tip 12 such that tip 12 does not contact any dispensed liquid medicament. Additionally, the tapered walls of reservoir 304 can be wider than tip 12, such that the sides of tip 12 do not contact the sides of reservoir 304 or any medicament that may be disposed along the reservoir wall.

A wide variety of inhalers or aerosolizers may be used to aerosolize the dispensed liquid. Exemplary aerosol generators that may be used in such inhalers are also described in U.S. Pat. Nos. 6,629,646; 6,926,208; 7,108,197; 5,938,117; 6,540,153; 6,540,154; 7,040,549; 6,921,020; 7,083,112; 7,628,339; 5,586,550; 5,758,637; 6,085,740; 6,467,476; 6,640,804; 7,174,888; 6,014,970; 6,205,999; 6,755,189; 6,427,682; 6,814,071; 7,066,398; 6,978,941; 7,100,600; 7,032,590; 7,195,011, and in U.S. Patent Publication Nos. 2011/0168172 and 2001/0168170, all incorporated herein by reference. These references describe exemplary aerosol generators, ways to manufacture such aerosol generators, and ways to supply liquid for aerosol generators. Each is incorporated by reference for at least these features.

While it is preferable to utilize all of the liquid medicament in a given container due to the large cost associated with some medicaments, the effectiveness of delivering the proper dosage can begin to fall off as the volume of medicament falls below a certain threshold. In other words, when the level of liquid gets too low, the dispenser is unable to deliver the full unit dosage amount to the aerosolizer. In several trials this threshold was approximately 37 actuations for a 3 mL fill volume dispensing a metered volume of 50 μL. After this point, the user runs the risk of air mixing with the liquid medicament inside a dispensing mechanism, providing an incorrect dosage.

The containers described herein may optionally include one or more indicator marks that signal to a user when the container needs to be replaced. The containers may be constructed of a clear or transparent material so that the level of liquid in the container may be visualized. By comparing the line formed by the level or liquid with the indicator mark, the user can determine whether the level of liquid within the container has fallen below an acceptable level. If so, the user knows that the container should be replaced. The comparison is most easily accomplished by placing the proximal end of the container on a level surface and then peering through the container to ascertain whether the level of liquid has fallen below the indicator mark. While the container may still include some liquid, if the level is below the indicator mark, the level is too low for an acceptable dosing amount, and the container should be replaced.

As shown in FIGS. 12-17, some embodiments of the dispenser 2 may optionally include one or more marks along a side of the container 8, which could be in many forms including, but not limited to, a notch or ring that is optionally colored and/or formed by an embossed ridge or depressed notch in the container to provide a visual indication to a user that there is insufficient medicament remaining to ensure a reliable dosage. The color of the mark may be selected to help a user distinguish the liquid level from the and mark as the user peers through container 8. In some cases, two spaced apart marks can be used which function as crosshairs. In other words, if the liquid cannot be visualized through the cross hairs, the user knows that there is no longer a reliable volume of medicament remaining in the container 8.

In FIG. 12, container 8 includes a mark 30 that allows a user to identify when the level of liquid medicament falls below a recommended and/or reliable level. If the remaining liquid is below this mark, the user is instructed to discard the container and obtain a fresh container with a full dosage. Mark 30 can be a horizontal line around all or part of the sides of the container 8. Other embodiments of such indicators are shown in FIGS. 13-15. FIG. 13 shows a top mark 42 separated from a bottom mark 52 by a clear or otherwise transparent horizontal centerline 48 (which is typically the wall of container itself). When the level of the liquid falls below this centerline 48, a user knows that an unreliable volume of the liquid remains. Any size or shape of marks 42 and 52 can be used, and the clear line 48 may be positioned off-center in some embodiments. For example, FIG. 14 shows a long rectangular top mark 44 separated from a shorter rectangular bottom mark 54 by a clear horizontal line or space 50 positioned at a height to indicate a reliable volume level of the container 8. FIG. 15 shows an embodiment where the reliable volume is indicated by the liquid being above a bottom edge of a mark 46. Mark 46 can be any shape, such as a circle. Other types of marks may be used in conjunction with container 8 to determine a liquid level.

Figure 16:
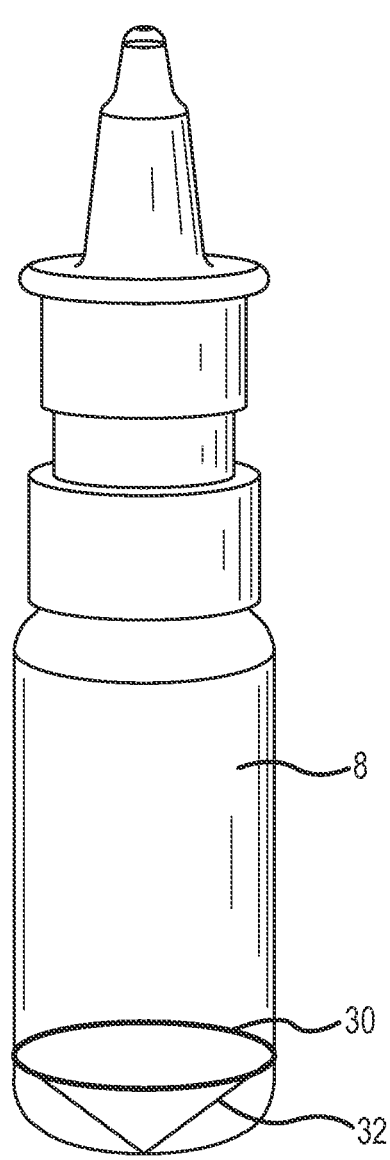
FIG. 16 is an embodiment of a dispenser having a last-use mark.
Figure 17:
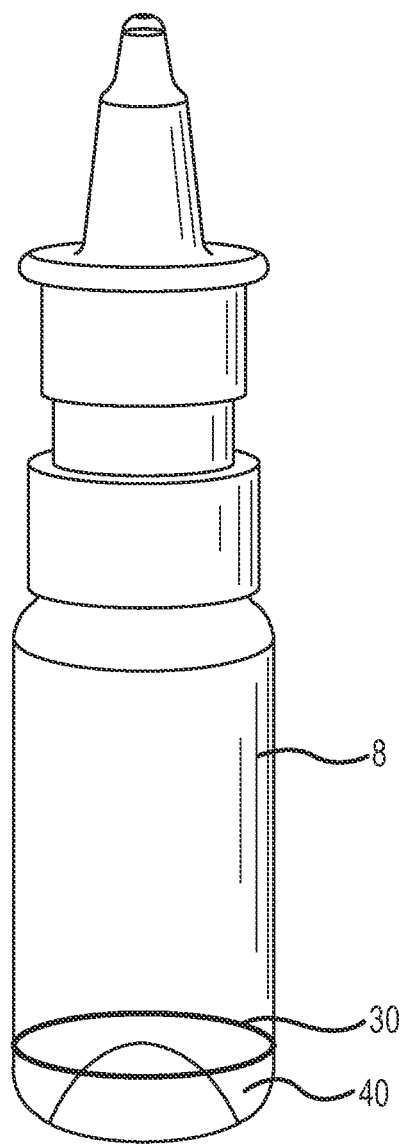
FIG. 17 is an embodiment of a dispenser having a last-use mark.

FIG. 16 depicts container 8 having a sloped bottom 32 along with mark 30. One reason for provided sloped bottom 32 is that is reduces the interior volume of container 8 at the proximal end. In turn, this allows mark 30 to be positioned vertically higher from the proximal end 4, thereby making mark 30 more easily distinguishable from proximal end 4. Other types of sloped bottoms may be used to raise the mark 30 from the proximal end 4. For example, FIG. 17 shows container 8 having a concave bottom surface 40 that allows the mark 30 to be raised while still indicating the same volume of liquid.

In some embodiments, a housing cap may also include a dip tube seat, which may aid in orienting the housing cap on the assembly line. The dip tube seat may optionally be configured to extend into a container or to be the same height as the housing cap. In some embodiments, the dip tube seat is formed to be shorter than housing cap. The housing cap's bottom surface may be configured to slope towards a base of the dip tube seat. One or more holes can be positioned at a base of the dip tube to allow the liquid medicament to access the delivery mechanism. In some embodiments, a slit that runs the entire longitudinal length of the dip tube seat may be used in place of or in conjunction with the holes for the liquid to pass through. By having the slit run the entire length of the dip tube seat, an efficient draining process can be achieved. Further, this configuration can ease the difficulties associated with manufacturing holes or slits in a dip tube seat.

The dip tube seat may be configured to have any shape of cross-section, for example, a circular cross-section. In some embodiments, the dip tube seat may be sealed or blocked at a top end, leaving only the hole or holes as a means for fluid communication between the container and dispensing mechanism. The dip tube seat may optionally have the sealing or blocking mechanism set beneath a top edge of the dip tube seat, which can aid in orienting the part on an assembly line during the manufacturing process.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A dispenser for supplying a metered volume of a liquid medicament to an aerosolizing device comprising:
    a container having a proximal end and a distal end, wherein the container is configured to store a volume of liquid medicament; and
    a dispensing mechanism coupled to the distal end of the container, the dispensing mechanism comprising a distal end terminating in a tip through which the liquid medicament is dispensed, wherein:
    the dispensing mechanism includes a housing cap comprising an interior bottom surface that comprises a sloped portion, the sloped portion being sloped toward an aperture and terminating proximate the aperture;
    the sloped portion is configured to direct the liquid medicament into the aperture, thereby aiding in the draining of the liquid medicament from the container into the dispensing mechanism;
    the dispensing mechanism operates to dispense a metered volume of the liquid medicament from the tip each time the dispensing mechanism is operated, and
    the distal end of the dispensing mechanism comprises an exterior surface that includes an interface comprising a protrusion that is spaced apart from the tip along a longitudinal axis of the dispenser, wherein the protrusion extends in a lateral direction beyond a periphery of the tip and interacts with an exterior of an opening in a housing of an inhaler while the container remains external to an exterior housing surface of the inhaler, wherein the protrusion is greater in dimension than the opening to limit an insertion depth of the tip into the opening of the housing such that the tip remains spaced apart by a fixed distance from an aerosol generator of the inhaler that is configured to receive the metered volume of the liquid medicament from the tip while preventing the tip from contacting tapered side walls of a reservoir of the inhaler, wherein the dispensing mechanism is actuated by applying compressive force to a proximal end of the dispenser and to the protrusion, wherein the compressive force is applied along the longitudinal axis, wherein the opening is formed within the exterior housing surface that defines an outer periphery of the inhaler, and wherein the exterior surface of the distal end of the dispensing mechanism tapers from the interface to the aperture.

2. The dispenser according to claim 1, wherein the interface comprises a seat.

3. The dispenser according to claim 1, wherein the interface comprises a shoulder, wherein the shoulder and the tip each have a diameter, the diameter of the shoulder being larger than the diameter of the tip.

4. The dispenser according to claim 1, further comprising an indicator line positioned near the proximal end that indicates to a user when there is insufficient liquid for recommended dispensing.

5. The dispenser according to claim 4, wherein a bottom surface of the proximal end is sloped to reduce the volume of the container at the proximal end such that the indicator line is spaced apart from the proximal end.

6. A method for manufacturing a dispenser for supplying a metered volume of a liquid medicament to an aerosolizing device, the method comprising:
    providing a container having a proximal end and a distal end, wherein the container is configured to store a volume of liquid medicament; and
    providing a dispensing mechanism that operates to dispense a metered volume of the liquid medicament from a tip of a distal end of the dispensing mechanism each time the dispenser is operated, the distal end of the dispensing mechanism comprising an interface having a protrusion that is spaced apart from the tip along a longitudinal axis of the dispenser, wherein the protrusion extends in a lateral direction beyond a periphery of the tip and interacts with an exterior of a housing of an inhaler to limit an insertion depth of the tip into an opening of the housing, wherein:

the dispensing mechanism includes a housing cap comprising an interior bottom surface that comprises a sloped portion, the sloped portion being sloped toward an aperture and terminating proximate the aperture; and the sloped portion is configured to direct the liquid medicament into the aperture, thereby aiding in the draining of the liquid medicament from the container into the dispensing mechanism; and the distal end of the dispensing mechanism comprises an exterior surface that includes the interface, wherein the interface comprises a protrusion that interacts with an opening in the housing of the inhaler while the container remains external to an exterior housing surface of the inhaler, wherein the protrusion is greater in dimension than the opening to limit the insertion depth of the tip into the opening of the housing such that the tip remains spaced apart by a fixed distance from an aerosol generator of the inhaler that is configured to receive the metered volume of the liquid medicament from the tip while preventing the tip from contacting tapered side walls of a reservoir of the inhaler, wherein the dispensing mechanism is actuated by applying compressive force to a proximal end of the dispenser and to the protrusion, wherein the compressive force is applied along the longitudinal axis, wherein the opening is formed within the exterior housing surface that defines an outer periphery of the inhaler, and wherein the exterior surface of the distal end of the dispensing mechanism tapers from the interface to the aperture.

7. The method according to claim 6, wherein the interface comprises a shoulder, wherein the shoulder and the tip each have a diameter, the diameter of the shoulder being larger than the diameter of the tip.

8. The method according to claim 6, wherein the dispenser is compressible such that the dispenser delivers a metered volume of liquid medicament upon application of a compressive force.

9. The method according to claim 6, wherein the container further comprises an indicator line positioned near the proximal end that indicates to a user when there is insufficient liquid for recommended dispensing.

10. The method according to claim 9, wherein a bottom surface of the proximal end is sloped to reduce the volume of the container at the proximal end such that the indicator line is spaced apart from the proximal end.

11. A method for supplying a metered volume of liquid medicament to an aerosolizing device, the method comprising:

providing a dispenser comprising:
a container having a proximal end and a distal end, wherein the container includes a volume of liquid medicament; and
a dispensing mechanism coupled to the distal end of the container, the dispensing mechanism having a distal end having an interface and terminating in a tip, wherein the interface comprises a protrusion that is spaced apart from the tip along a longitudinal axis of the dispenser and that extends in a lateral direction beyond a periphery of the tip, wherein the dispensing mechanism is actuated by applying compressive force to a proximal end of the dispenser and to the protrusion, wherein the compressive force is applied along the longitudinal axis, wherein:

the dispensing mechanism includes a housing cap comprising an interior bottom surface that comprises a sloped portion, the sloped portion being sloped toward an aperture and terminating proximate the aperture, wherein the distal end of the dispensing mechanism comprises an exterior surface that includes the interface, and wherein the exterior surface of the distal end of the dispensing mechanism tapers from the interface to the aperture; and the sloped portion is configured to direct the liquid medicament into the aperture, thereby aiding in the draining of the liquid medicament from the container into the dispensing mechanism;

providing an inhaler comprising:
a housing having a mouthpiece, the housing comprising an exterior surface that defines an outer periphery of the inhaler;
an opening in the exterior surface of the housing configured to receive the tip of the dispenser while the container of the dispenser remains external to the exterior surface of the housing;
a vibratable mesh disposed within the housing and spaced a distance from the opening that is configured to aerosolize the metered volume of liquid medicament; and
a reservoir having tapered walls that are configured to direct the liquid medicament onto the vibratable mesh, the tapered walls being wider than the opening and the tip of the dispensing mechanism;

inserting the tip into the opening of the inhaler until the interface of the distal end contacts the exterior surface of the housing outside of the opening to limit an insertion depth of the tip to maintain the tip a distance from the vibratable mesh and such that the tip does not contact the tapered walls of the reservoir, wherein the interface comprises a protrusion that interacts with the opening in the housing of the inhaler and is greater in dimension than the opening to limit the insertion depth of the tip into the opening of the housing such that the tip remains spaced apart by the distance from the vibratable mesh; and compressing the dispenser to deliver a metered volume of the liquid medicament from the tip to the vibratable mesh while the tip remains spaced apart by the distance.

12. The method according to claim 11, wherein compressing the dispenser comprises applying a compressive force to both the inhaler and the dispenser.

13. The method according to claim 11, further comprising placing the inhaler on a support surface, wherein compressing the dispenser comprises applying a compressive force to the dispenser.

14. The method according to claim 11, wherein the inhaler further comprises a cover that seals the opening and the vibratable mesh, and further comprising moving the cover to expose the opening and the vibratable mesh.

15. The method according to claim 11, wherein the container comprises an indicator line positioned near the proximal end that indicates to a user when there is insufficient liquid for recommended dispensing.

16. The method according to claim 11, wherein the interface contacts the housing such that the tip is maintained at a distance from the mesh such that the tip is not in contact with the dispensed metered volume of the liquid medicament.

17. A dispenser for supplying a metered volume of a liquid medicament to an aerosolizing device comprising:
- a container having a proximal end and a distal end, wherein the container is configured to store a volume of liquid medicament, and wherein at least a portion of the proximal end is constructed of a transparent material to permit a level of the liquid to be visualized from outside of the container;
- an indicator mark positioned near the proximal end that indicates to a user when the level of the liquid has fallen below an acceptable level; and
- a dispensing mechanism coupled to the distal end of the container, the dispensing mechanism comprising a distal end terminating in a tip through which the liquid medicament is dispensed, wherein the dispensing mechanism operates to dispense a metered volume of the liquid medicament each time the dispensing mechanism is operated, wherein:
  - the dispensing mechanism includes a housing cap comprising an interior bottom surface that comprises a sloped portion, the sloped portion being sloped toward an aperture and terminating proximate the aperture;
  - the sloped portion is configured to direct the liquid medicament into the aperture, thereby aiding in the draining of the liquid medicament from the container into the dispensing mechanism; and
  - the distal end of the dispensing mechanism includes an interface having a protrusion that is spaced apart from the tip along a longitudinal axis of the dispenser, wherein the protrusion extends in a lateral direction beyond a periphery of the tip and interacts with an exterior of a housing of an inhaler to limit an insertion depth of the tip into an opening of the housing; and
  - the distal end of the dispensing mechanism comprises an exterior surface that includes the interface, wherein the interface comprises a protrusion that interacts with the opening in the housing of the inhaler while the container remains external to an exterior housing surface of the inhaler, wherein the protrusion is greater in dimension than the opening to limit the insertion depth of the tip into the opening of the housing such that the tip remains spaced apart by a fixed distance from an aerosol generator of the inhaler that is configured to receive the metered volume of the liquid medicament from the tip while preventing the tip from contacting tapered side walls of a reservoir of the inhaler, wherein the dispensing mechanism is actuated by applying compressive force to a proximal end of the dispenser and to the protrusion, wherein the compressive force is applied along the longitudinal axis, wherein the opening is formed within the exterior housing surface that defines an outer periphery of the inhaler, and wherein the exterior surface of the distal end of the dispensing mechanism tapers from the interface to the aperture.

18. The dispenser according to claim 17, wherein the indicator mark comprises a horizontal line extending along at least a portion of the container.

19. The dispenser according to claim 17, wherein a bottom surface of the proximal end of the container is sloped to reduce the volume of the container at the proximal end such that the indicator line is spaced apart from the proximal end.

20. The dispenser according to claim 17, wherein the indicator mark comprises a top portion and a bottom portion that are separated by a transparent portion, and wherein when a level of the liquid medicament falls below the transparent portion there is insufficient liquid for a recommended dispensing.

21. The dispenser according to claim 20, wherein the top portion and the bottom portion each comprise a half circles, and the transparent portion comprises a clear line.

22. The dispenser according to claim 20, wherein the top portion and the bottom portion comprise rectangles, and the transparent portion comprises a clear line.

* * * * *